(12) United States Patent
Montagnino et al.

(10) Patent No.: US 6,245,024 B1
(45) Date of Patent: Jun. 12, 2001

(54) BLOOD PRESSURE CUFF WITH TENSION INDICATOR

(75) Inventors: James G. Montagnino, St Charles, IL (US); Mark A. Castracane, Hattiesburgh, MI (US)

(73) Assignee: Sunbeam Products, Inc., Boca Raton, FL (US)

( * ) Notice: Subject to any disclaimer, the term of this patent is extended or adjusted under 35 U.S.C. 154(b) by 0 days.

(21) Appl. No.: 09/482,821

(22) Filed: Jan. 13, 2000

(51) Int. Cl.$^7$ ........................................... A61B 5/00
(52) U.S. Cl. ............................. 600/499; 606/202
(58) Field of Search ............... 600/499; 606/202

(56) References Cited

U.S. PATENT DOCUMENTS

| | | | |
|---|---|---|---|
| 3,968,788 | * 7/1976 | Hopkins | 600/499 |
| 4,901,732 | * 2/1990 | Williams | 600/499 |
| 4,920,971 | * 5/1990 | Blessinger | 600/499 |
| 5,746,213 | 5/1998 | Marks | 128/686 |

* cited by examiner

Primary Examiner—Robert L. Nasser
(74) Attorney, Agent, or Firm—Kramer Levin Naftalis & Frankel LLP.

(57) ABSTRACT

A blood pressure cuff which, when the cuff is being applied to the patient, automatically indicates when the proper amount of tension in the cuff has been reached. The blood pressure cuff includes a tension sensor disposed on an end which the user grips, constructed of elastomeric or elastic material, including accordion-like ridges. The ridges include a graphic which is partially or substantially hidden when less then the proper amount of tension is applied to the blood pressure cuff, and which is substantially viewable when the proper amount of tension is applied to the blood pressure cuff. The tension sensor may include an indicator area which is substantially hidden by a set of folds until a pre-set amount of tension is applied.

22 Claims, 3 Drawing Sheets

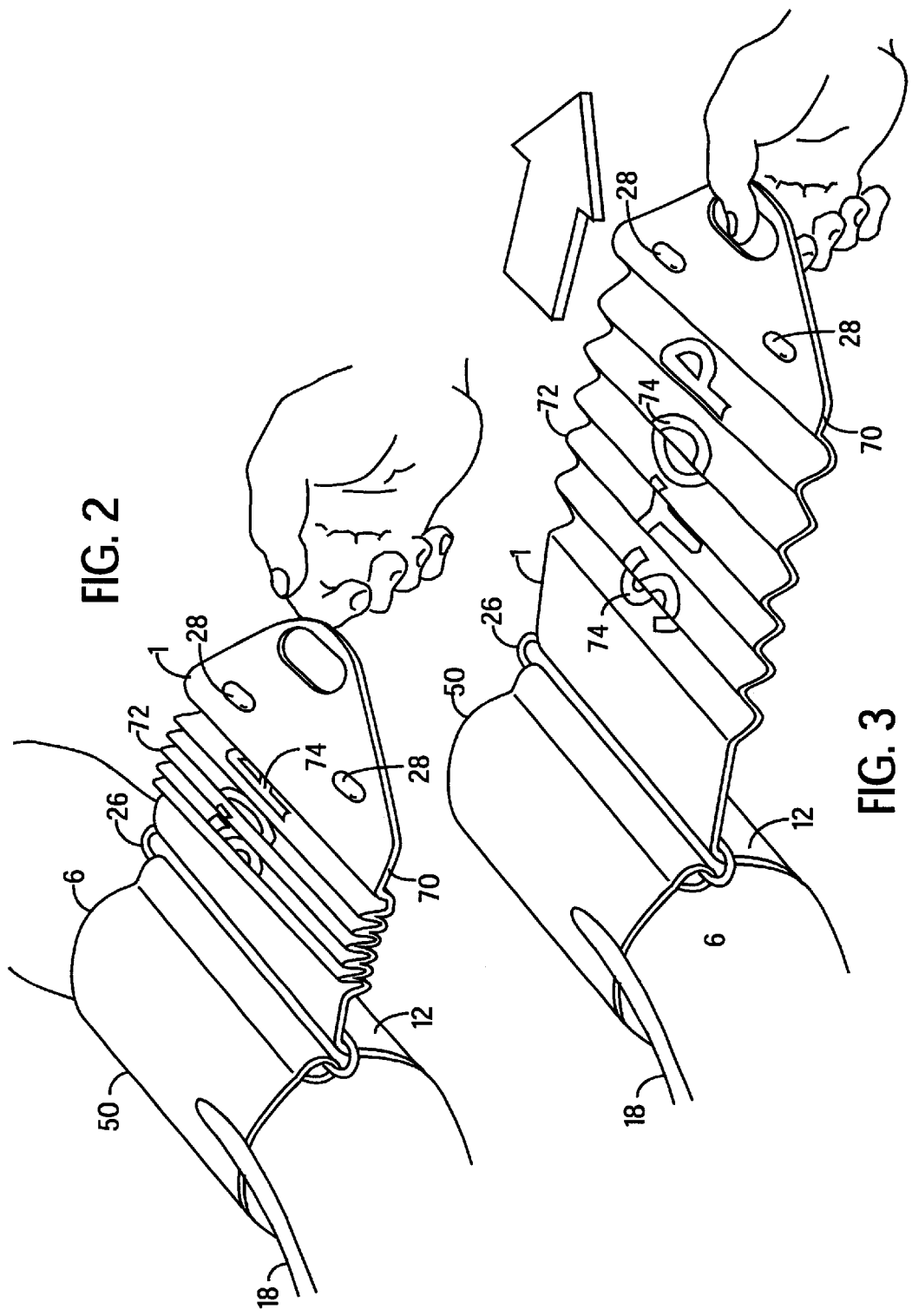

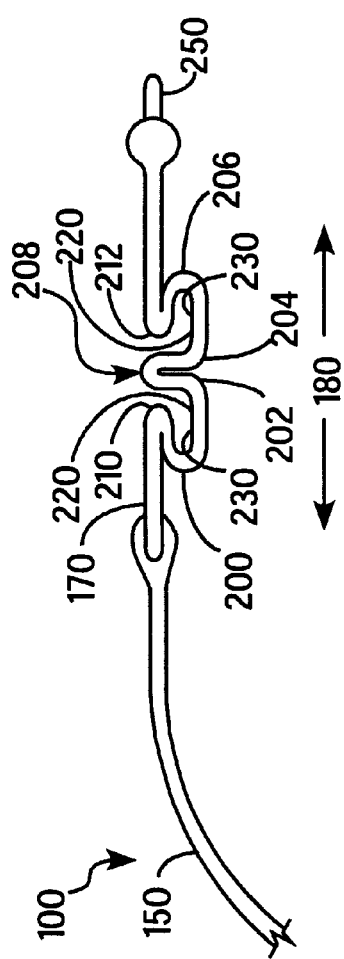
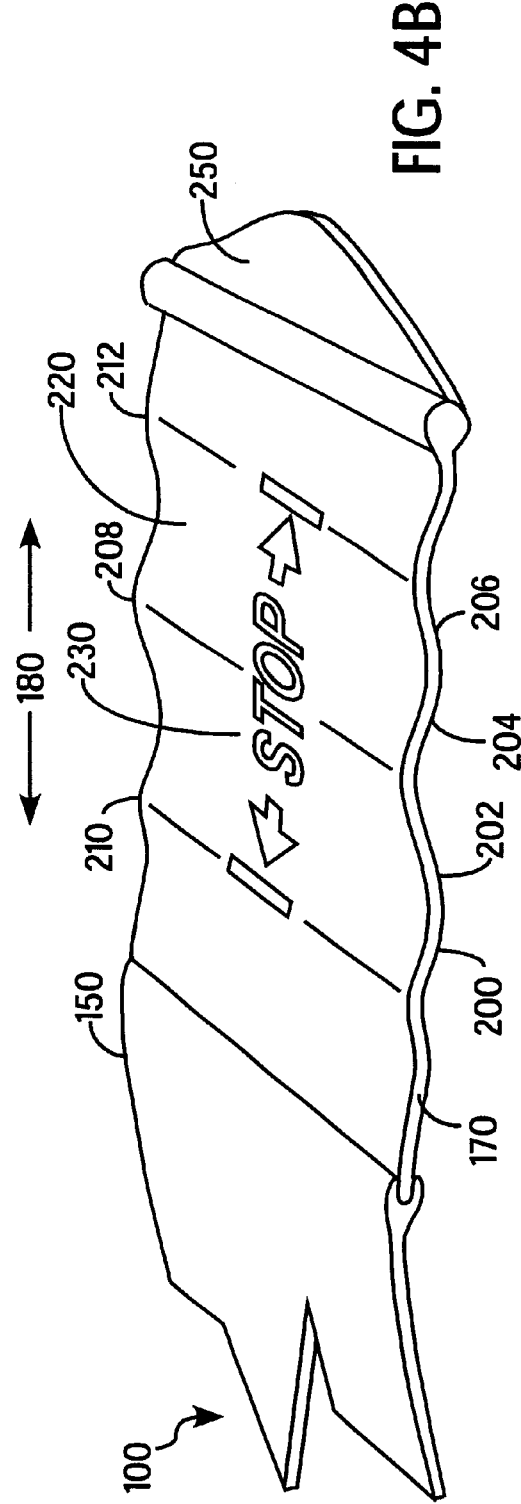

BLOOD PRESSURE CUFF WITH TENSION INDICATOR

FIELD OF THE INVENTION

The present invention relates to blood pressure cuffs; more specifically to blood pressure cuffs providing an indication of the proper tension for blood pressure measurement.

BACKGROUND INFORMATION

A common method of measuring the blood pressure of a human patient involves wrapping an inflatable cuff around the patient's arm. An operator inflates the cuff thereby applying pressure to the arm. The operator then slowly deflates the cuff while measuring the blood pressure. The blood pressure may be measured by, for example, listening to blood flow using a stethoscope as the cuff is deflated. It is common for such blood pressure cuffs to be provided to a patient who must periodically monitor his or her own blood pressure at home. In such a case the patient must be trained in the proper use of the blood pressure measuring device.

Such an inflatable cuff typically includes an inflatable bladder formed, for example, of an elastic sheet such as a rubber sheet or a vinyl sheet contained within a non-stretch belt-like bag. The belt-like bag may be constructed of cloth or other material. Typically, the inflatable bladder is disposed towards one end of the belt-like bag, and extends approximately half way towards the center of the blood pressure cuff, so that a portion of the belt-like bag not surrounding the inflatable bladder may wrapped around the patient's arm to secure the cuff to the arm. The bladder may be constructed of air-tight, flexible, bio-compatible material such as PVC. Velcro™ patches or other connection means may be used to secure one portion of the belt-like bag to itself.

Typically the inflatable bladder is connected to an air pump which may be operated by hand to inflate the inflatable bladder. The air pump is connected to the inflatable bladder by a flexible air-tight tube or piping. The air pump is connected to a pressure sensor which provides an indication of the pressure inside the inflatable bladder, readable by a human operator. Such a pressure sensor may include a visible dial type gauge. The air pump includes a deflation-control valve device having a control such as an adjustable knob. The control may be adjusted so that the deflation-control valve allows inflation or variable amounts of deflation.

One important part of the procedure for measuring blood pressure is applying the cuff to the arm. The portion of the cuff surrounding the inflatable bladder is placed on the patient's arm, and the cuff is wrapped around the patient's arm. The cuff should be wrapped around the patient's arm with a certain amount of tension. Typically, a user will wrap the cuff, using his or her own tactile sense to gauge the amount of tension applied to the cuff, and attach a portion of the cuff to itself using, for example, Velcro patches often resulting in improper wrapping of the cuff. Improper cuff tension results in an incorrect blood pressure measurement cycle. For example, if too little tension is provided, too much air must be pumped into the bladder and the measurement cycle may be unnecessarily long, resulting in an inaccurate measurement. If too much tension is provided, the blood vessels in the arm may be compressed prior to the bladder being inflated, which instead should be controlled by the inflation of the bladder, also resulting in an inaccurate measurement.

A patient who is not a trained health professional and who is measuring his or her own blood pressure using such a device may fail to apply proper tension to such a cuff. Even health professionals using such devices may apply the cuff with inaccurate tension.

Therefore, there exists a need for a blood pressure cuff which a user may apply while being assured that the proper amount of tension is being used for placement of the cuff.

SUMMARY OF THE INVENTION

An exemplary embodiment of the present invention provides for a cuff used for blood pressure measurement which, when the cuff is being applied to the patient, automatically indicates when the proper amount of tension in the cuff has been reached. The blood pressure cuff includes a tension sensor disposed on the end of the cuff which the user grips, constructed of elastomeric or other elastic material, including accordion-like ridges. The ridges include a graphic which is partially or substantially hidden when less then the proper amount of tension is applied to the blood pressure cuff, and which is substantially viewable when the proper amount of tension is applied to the blood pressure cuff. Alternately, the tension sensor may include an indicator area which is substantially hidden by a set of folds until a pre-set amount of tension is applied.

BRIEF DESCRIPTION OF THE DRAWINGS

FIG. 2 depicts a blood pressure cuff according to an exemplary embodiment of the present invention after the blood pressure cuff is installed but before tension is applied to the blood pressure cuff.

FIG. 3 depicts a blood pressure cuff according to an exemplary embodiment of the present invention after the blood pressure cuff is installed, and after tension has been applied to the blood pressure cuff.

FIG. 4a depicts a blood pressure cuff according to another exemplary embodiment of the present invention.

FIG. 4b depicts the blood pressure cuff of FIG. 4a according to an exemplary embodiment of the present invention after a threshold amount of tension has been applied to the blood pressure cuff.

DETAILED DESCRIPTION OF THE INVENTION

Figure 1:
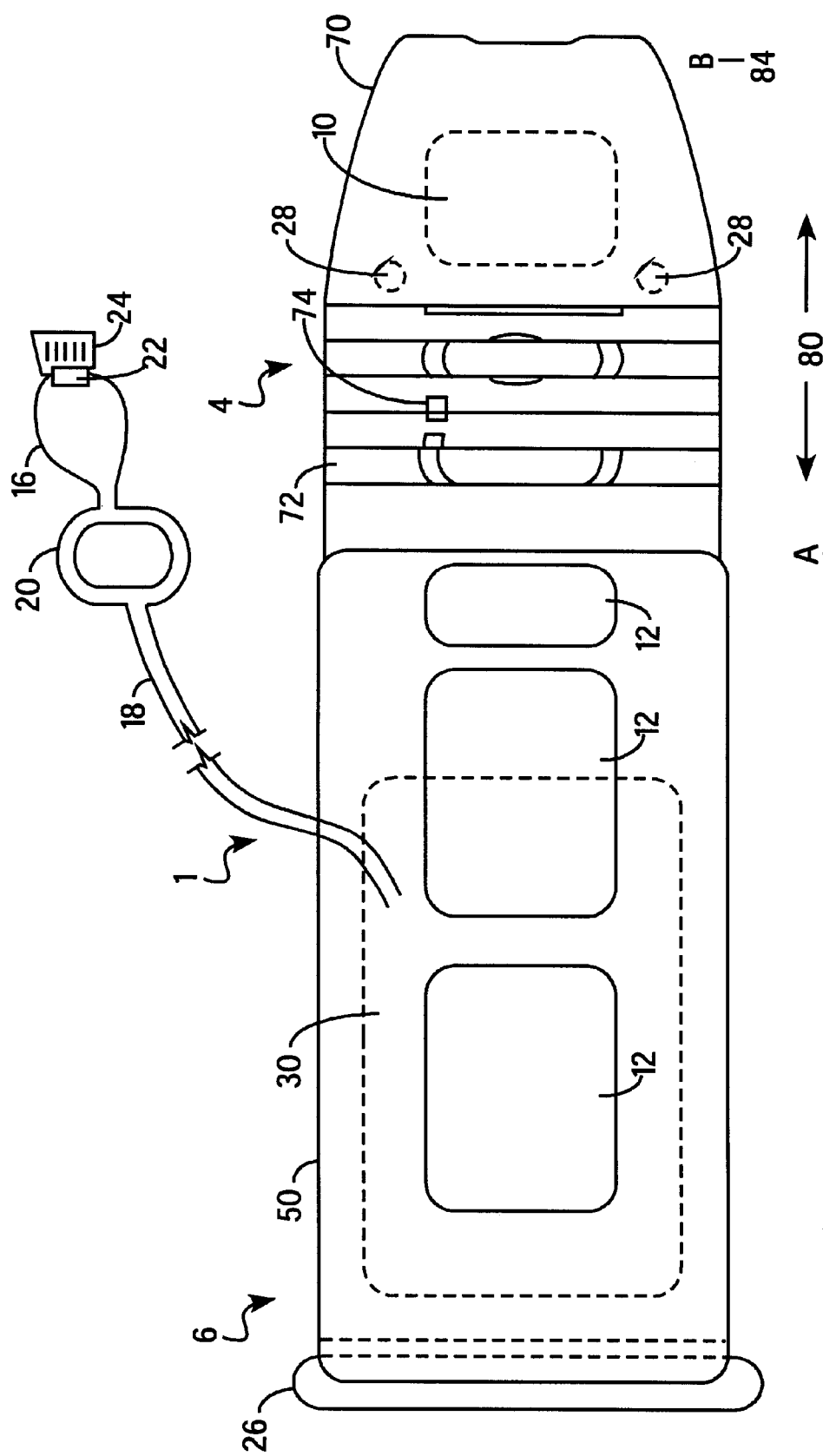
FIG. 1 is a diagram of a blood pressure cuff according to an exemplary embodiment of the present invention.

In the following description, various aspects of the present invention will be described. For purposes of explanation, specific configurations and details are set forth in order to provide a thorough understanding of the present invention. However, it will also be apparent to one skilled in the art that the present invention may be practiced without the specific details. Furthermore, well known features are omitted or simplified in order not to obscure the present invention.

FIG. 1 is a diagram of a blood pressure cuff according to an exemplary embodiment of the present invention. The blood pressure cuff 1, having a first end 4 and a second end 6, includes a belt-like or sleeve-like substantially non-stretchable bag 50. The blood pressure cuff 1 has at its first end 4 a stretchable tension sensor 70 for indicating to a user the amount of tension used to apply the blood pressure cuff 1 to the patient's arm. In an exemplary embodiment the tension sensor 70 is disposed at the end of the blood pressure cuff 1 which the user grips while wrapping and providing tension to the blood pressure cuff 1.

The bag 50 encloses an inflatable bladder 30 formed, for example, of an elastic sheet of air-tight, flexible, bio-compatible material such as PVC. The non-stretch bag 50 may be constructed of, for example, nylon cloth. The inflatable bladder 30 is disposed towards one end of the non-stretch bag 50, and extends approximately half way through the blood pressure cuff 1, so that a portion of the non-stretch bag 50 not surrounding the inflatable bladder 30 may wrapped around the patient's arm and used to secure the cuff to the arm. Preferably, all materials and dyes used to construct the blood pressure cuff 1 are bio-compatible.

In an exemplary embodiment, the blood pressure cuff 1 includes one or more hook Velcro™ patches 10 located near the first end 4 on the tension sensor 70, and one or more loop Velcro™ patches 12 disposed along another portion of the blood pressure cuff 1, for securing the first end 4 of the blood pressure cuff 1 to another portion of the blood pressure cuff 1. In the view depicted in FIG. 1, hook Velcro patches 10 are shown on the far, back side of the blood pressure cuff 1 and the loop Velcro patches 12 are shown on the near, front side. The hook Velcro patches 10 may include one or more patches; typically the loop Velcro patches 12 include more than one patch, or one large patch, so that the first end 4 may be attached at a number of places along blood pressure cuff 1, according to varying arm sizes. Other means of attaching a portion of the blood pressure cuff 1 to itself may be used.

The inflatable bladder 30 is connected to an air pump 16 which may be operated, for example, by hand to inflate the inflatable bladder 30. The air pump 16 is connected to the inflatable bladder 30 by a flexible air-tight tube 18. The air pump 16 is connected to a pressure sensor 20 which provides an indication of the pressure inside the inflatable bladder 30, which is readable by a human operator. The pressure sensor 20 may include a visible dial type gauge, but may include other types of sensors, such as a sensor with a digital readout. The air pump 16 includes a deflation-control valve 22 with a control 24. In an exemplary embodiment, the control 24 is a knob. The control 24 may be adjusted so that the deflation-control valve 22 allows inflation using the air pump, slow deflation, or fast deflation. Other methods of allowing inflation and deflation of the inflatable bladder may be used, including known blood pressure cuff automatic inflation mechanisms.

In an exemplary embodiment, the tension sensor 70 is a sheet constructed of elastomeric material, such as bio-compatible plastic, having at least a portion including a set of accordion-like or convoluted ridges 72. In an alternate embodiment, the tension sensor 70 may be constructed of any stretchable or expandable material. When seen from a side view, the tension sensor 70 is a sheet with at least a portion of the sheet including the ridges 72 appearing as a wavy portion. Alternately, the entire tension sensor 70 may be ridged or ribbed. The bag 50 may be attached to the tension sensor 70 by, for example, adhesive or sewing or may otherwise enclose tension sensor 70. When the ridges 72 and the tension sensor 70 are not under tension, the ridges 72 compress. When a pre-set amount of tension is applied to the tension sensor 70 at end B 84, for example when the tension sensor 70 is pulled according to the directions indicated by arrows 80, the ridges 72 in the tension sensor 70 stretch. In an exemplary embodiment, the ridges 72 are integral with the tension sensor 70, and are manufactured from the same sheet of elastomeric material. In alternate embodiments, the tension sensor 70 or ridges 72 may be constructed of any stretchable or expandable material, such as metal or fabric, and furthermore may be separate parts.

In an exemplary embodiment, a graphic 74 is imprinted on the ridges 72 of the tension sensor 70. The graphic 74 is applied using ink, dye, or other substance, and is fully visible only when the ridges 72 are substantially stretched. In FIG. 1, the graphic 74 is not fully visible thus indicating that further tension must be applied by the user prior to wrapping the cuff around the users arm. When the proper tension is applied, the graphic 74 provides an obvious indication that the user has applied a proper amount of tension to the tension sensor 70 and blood pressure cuff 1. The graphic 74 may provide, for example, a written message or another indication. In FIG. 1, the graphic 74 is applied to both sides of the ridges 72; only one side is visible in FIG. 1. When less than a predetermined amount of tension is applied to the tension sensor 70, the graphic 74 is either partially or substantially hidden. If the graphic 74 is partially hidden, it may be viewed, but it is obvious to a viewer that the tension sensor 70 is not under a predetermined amount of tension. In alternate embodiments, the graphic may be other types indicators, such as material that changes color when stretched or a device that changes appearance when stretched.

In an exemplary embodiment, the amount of tension required to stretch the ridges 72 on the tension sensor 70 enough to display the graphic 74 corresponds approximately to the proper amount of tension which should be applied by the blood pressure cuff 1 (and thus the tension sensor 70) to the user's arm prior to inflation of the bladder 30 to accurately measure blood pressure. In an exemplary embodiment, this range is between four and six pounds of tension, with five pounds being preferred. In alternate embodiments and for various physical conditions of users, other amounts and ranges of tension may be used. The amount of tension required to stretch the ridges 72 enough to display the graphic 74 may be varied by altering or selecting, for example, the materials used to form the ridges 72 and the tension sensor 70, the method of manufacturing the ridges 72 and the tension sensor 70, the dimensions and thickness of the ridges 72 and the tension sensor 70, and the angles of the ridges 72. Alternately, the stretchability of the tension sensor may be altered or reduced by, for example, adding materials or structures such as metal springs to the tension sensor. In such manners the amount of tension may be pre-set by the manufacturer to conform to the amount of tension required for accurate blood pressure measurement.

The blood pressure cuff 1 also includes, for example, a D-ring 26, for attaching the first end 4 of the blood pressure cuff to the second end 6. The D-ring 26 is attached to the blood pressure cuff 1 by feeding one end of the non-stretch bag 50 through the D-ring 26 and attaching the non-stretch bag 50 to itself. The D-ring 26 may be manufactured of a rigid material such as stainless steel. To apply the blood pressure cuff 1 to a patient's arm, the first end 4, including the tension sensor 70, is fed through the D-ring 26, pulled tight, and folded back along a portion of the blood pressure cuff 1. Typically, the user will not pull the first end 4 through the D-ring 26 past the junction of the tension sensor 70 and the non-stretch bag 50; a barrier or bump may be provided to prevent this occurrence. The portion of the first end 4 which contacts the D-ring 26 may be smooth to reduce the friction between the first end 4 and the D-ring 26. Such a portion may be on the tension sensor 70, or may be, for example, part of the blood pressure cuff 1 covered by the loop Velcro patches 12. Furthermore, the first end 4 may be narrowed or pointed to enable easy entry into the D-ring 26. A portion of the hook Velcro patches 10 connect to a portion of the loop Velcro patches 12 to secure the blood pressure cuff 1.

The first end 4 includes bumps 28, for example, material such as plastic or metal, for preventing the first end 4 from quickly passing through the D-ring 26 in case the first end 4 slips out of the user's hand during application. The bumps 28 may be integral with the tension sensor 70. The bumps 28 are small enough to allow the first end 4 to fit through the D-ring 26 but are large enough to momentarily stop the first end 4 from slipping out of the D-ring 26 if the user accidentally looses a grip on the first end 4. In the view of FIG. 1, the bumps 28 are disposed on the back side of blood pressure cuff 1. Alternately, the bumps may be any structure designed to present a temporary barrier, such as a ridge.

To operate the blood pressure cuff 1 the user (which may be the patient, if the patient is taking his or her own blood pressure) places the second end 6 on the patient's arm, so that when the inflatable bladder 30 is inflated all or substantially all of the inflatable bladder 30 is against the patient's arm. The user wraps the blood pressure cuff 1 around the patient's arm. The user passes the first end 4 through the D-ring 26 and pulls the first end 4 with a certain amount of tension. The proper amount of tension is indicated when the graphic 74 is substantially visible. The user then folds the first end 4 back along a portion of the blood pressure cuff 1. The hook Velcro patches 10 connect to a portion of the loop Velcro patches 12 to secure the blood pressure cuff 1, at a predetermined amount of tension to the patient's arm. The user may then operate the air pump 16, deflation-control valve 22 and pressure sensor 20, in conjunction with a stethoscope, according to known methods. The tension sensor may be designed to open more rapidly when a tension threshold has been reached. For example, the tension sensor may gradually expand with increasing tension, and when the lowest tension considered proper for accurate blood pressure measuring has been reached, the tension sensor may expand more rapidly to indicate that the desired tension level or range has been reached.

In alternate embodiments, other systems or methods may be used to measure blood pressure using the cuff of the present invention. For example, an automatic pumping and deflation mechanism may be connected to the bladder, or an electronic measuring mechanism may measure calculate blood pressure.

FIG. 2 depicts a blood pressure cuff according to an exemplary embodiment of the present invention after the blood pressure cuff is installed but before tension is applied to the blood pressure cuff. In the view of FIG. 2, the blood pressure cuff 1 has been wrapped around the patient's arm and has pulled the first end 4 through the D-ring 26. Since the ridges 72 and the tension sensor 70 are not under enough tension, the ridges 72 are compressed, accordion style, and the graphic 74 is substantially hidden in the folds of the ridges 72. In FIG. 2, the graphic 74 is applied to both sides of the ridges 72; only one side is visible in FIG. 2. The user may apply tension to the blood pressure cuff 1 and still not cause the ridges 72 and the tension sensor 70 to extend or open; until the ridges 72 are under a pre-set amount of tension, they remain substantially folded, and the graphic 74 substantially hidden in the folds of the ridges 72. Until the tension sensor 70 stretched enough to fully display the graphic 74, the user knows that the blood pressure cuff 1 is not under enough tension to enable proper a blood pressure measurement.

FIG. 3 depicts a blood pressure cuff according to an exemplary embodiment of the present invention after the blood pressure cuff is installed, and after tension has been applied to the blood pressure cuff. In the view of FIG. 3, the blood pressure cuff 1 has been wrapped around the patient's arm and has pulled the first end 4 through the D-ring 26. The user has pulled on the tension sensor 70 with enough tension so that the ridges 72 and the tension sensor 70 have expanded. In an exemplary embodiment, this pre-set tension is between four and six pounds of pressure, with five pounds being preferred. Since the ridges 72 and the tension sensor 70 have expanded and substantially flattened, the graphic 74 is substantially viewable. In FIG. 3, the graphic 74 is applied to both sides of the ridges 72; only one side is visible in FIG. 3.

When the ridges 72 and the tension sensor 70 display the graphic 74, the user knows that enough tension is being applied to the blood pressure cuff, and the user should not increase the amount of tension, but should instead fold the first end 4 back along the blood pressure cuff to affix the first end 4 to the blood pressure cuff. The display of the graphic 74 indicates that if more tension is applied to the blood pressure cuff, an accurate blood pressure measurement may not occur. Note that in an exemplary embodiment the ridges 72 and the tension sensor 70 appear substantially similar whether adequate tension or too much tension is applied; therefore, the user may be instructed to stop increasing tension when the graphic 74 appears.

In an alternate embodiment, the blood pressure cuff may include a tension sensor which includes an indicator substantially hidden by folds, convolutions, or the like, and which snaps open or unfolds to reveal the indicator area when a tension threshold is reached. FIG. 4*a* depicts a blood pressure cuff according to an exemplary embodiment of the present invention. Referring to FIG. 4*a*, the blood pressure cuff 100 includes a belt-like or sleeve-like substantially non-stretchable bag 150. The non-stretch bag 150 may be constructed of, for example, nylon cloth. The blood pressure cuff 100 includes a stretchable tension sensor 170 for indicating to a user the amount of tension used to apply the blood pressure cuff 100 to a patient's arm. In such an embodiment the tension sensor 170 is disposed at the end of the blood pressure cuff 100 which the user grips while wrapping and providing tension to the blood pressure cuff 100.

The bag 150 encloses an inflatable bladder (not shown) for providing pressure to a patient's arm during blood pressure measurement. The inflatable bladder is connected to conventional structures (not shown) for measuring blood pressure, such as an air pump, a pressure sensor, a pressure gauge, and a deflation-control valve.

In one embodiment, the tension sensor 170 is a sheet constructed of elastomeric material, such as bio-compatible plastic. The tension sensor 170 includes, for example, folds 200, 202, 204, 206, 208, 210 and 212. The folds 200–212 define an indicator area 220, on which is imprinted an indicator image 230. When the tension sensor 170 is under less tension than a pre-set threshold, the folds 202–212 are folded or compressed to substantially conceal the indicator image 230. Preferably the pre-set threshold corresponds to the optimum tension which is to be applied to the cuff 100 for measuring blood pressure, and is between four and six pounds of tension, with five pounds being preferred. The bag 150 may be attached to the tension sensor 170 by, for example, adhesive or sewing.

When the folds 200–212 and the tension sensor 170 are not under tension, the folds 200–212 compress and are folded, as depicted in FIG. 4a. When a pre-set amount of tension is applied to the tension sensor 170, the tension sensor 170 is pulled according to the directions indicated by arrows 180, and the folds 200–212 stretch to reveal the indicator image 230. Preferably the folds 200–212 open substantially at once, with a motion akin to a snapping motion. A user may grip area 250 to provide tension to the cuff 100 and the tension sensor 170. In one exemplary embodiment, the folds 200–212 are integral with of the tension sensor 170, and are manufactured from the same sheet of elastomeric material. In alternate embodiments, the tension sensor 170 may be constructed of any stretchable or expandable material, and may have a different number or configuration of folds or convolutions.

In an exemplary embodiment as in FIG. 4a, shown in when the folds 200–212 are folded, a portion of the material of the tension sensor 170 forms two folded lobes separated by a set of folds 202, 204 and 208. The two folded lobes substantially conceal the indicator image 230. In alternate embodiments other combinations of folds forming other patterns of compressed or hidden material may be used.

The indicator image 230 is applied using ink, dye, or other substance, and is fully visible only when the folds 200–212 are substantially stretched. In FIG. 4a, the indicator image 230 is not fully visible thus indicating that additional tension is required to properly wrap the cuff. Display of the indicator image 230 provides an obvious indication that the user has applied a proper amount of tension to the tension sensor 170 and to the blood pressure cuff 100.

FIG. 4b depicts the blood pressure cuff of FIG. 4a according to an exemplary embodiment of the present invention after a threshold amount of tension has been applied to the blood pressure cuff. Referring to FIG. 4b, a user has gripped area 250 to provide tension to the cuff 100 and tension sensor 170. The user has applied at least a pre-set amount of tension to the tension sensor 170 along the directions indicated by arrows 180. The folds 200–212 have opened to reveal the indicator image 230.

The amount of tension required to stretch the folds 200–212 enough to display the indicator image 230 may be varied by altering or selecting the materials used to form the folds 200–212 and the tension sensor 170, the method of manufacturing the folds 200–212 and the tension sensor 170, the dimensions and thickness of the folds 200–212 and the tension sensor 170, and the angles of the folds 200–212. Alternately, the stretchability of the tension sensor 170 may be altered or reduced by, for example, adding materials or structures such as metal springs to the tension sensor 170. In such manners the amount of tension may be pre-set by the manufacturer to conform to the amount of tension required for accurate blood pressure measurement.

The blood pressure cuff according to various embodiments of the present invention provides an indication of when the proper tension for taking blood pressure is reached and makes it more likely that a patient self-administering a blood pressure test will take an accurate reading. Even health professionals may benefit from the use of the blood pressure cuff of the present invention.

While the blood pressure cuff of the present invention is described with respect to specific embodiments, it should be noted that the present invention may be implemented in different manners and be used with different applications. The graphic or indicator image may be any sort of indication that the proper pressure had been applied, and need not be a written message. Alternately, a graphic need not be included, and the user may simply detect adequate pressure when the tension indicator stretches.

In alternate embodiments the structure of the tension sensor may be other than the accordion sheet or the folded sheet depicted, and may not require a ridged or ribbed portion. The tension sensor may be any sort of device or material indicating when a certain amount of tension is applied, such as an assembly with a spring or a sheet of elastic fabric. The tension sensor may be integral with or constructed from the same piece as the cuff or a portion of the cuff. The tension sensor may be an electronic gauge providing an indication that an optimum tension range has been reached. Furthermore, the tension sensor of the present innovation may be used with any sort of cuff or band. For example, the present invention may provide a tension sensor for a flexible splint.

What is claimed is:

1. A blood pressure cuff, comprising:
    a sleeve;
    an inflatable bladder disposed in the sleeve; and
    a tension sensor coupled to the sleeve.
2. The blood pressure cuff of claim 1 comprising a ridged portion disposed on the tension sensor.
3. The blood pressure cuff of claim 2 wherein the tension sensor displays a message when a predetermined amount of tension is applied to the tension sensor.
4. The blood pressure cuff of claim 3 wherein the tension sensor includes an elastomeric material.
5. The blood pressure cuff of claim 4 wherein the inflatable bladder is coupled to an air pump and valve assembly.
6. The blood pressure cuff of claim 2 comprising a graphic imprinted on the ridged portion.
7. The blood pressure cuff of claim 6 wherein the graphic is partially hidden when less than a predetermined amount of tension is applied to the tension sensor and wherein the graphic is substantially viewable when more than a predetermined amount of tension is applied to the tension sensor.
8. The blood pressure cuff of claim 7 wherein the tension sensor includes an elastomeric material.
9. The blood pressure cuff of claim 1 wherein the tension sensor indicates the tension applied to the blood pressure cuff when the cuff is being applied to a patient's arm.
10. The blood pressure cuff of claim 1 wherein the tension sensor includes a plurality of folds, wherein when the tension sensor is under a certain range of tension the folds are substantially compressed, and wherein when the tension sensor is under at least a pre-set amount of tension the folds are substantially open.
11. The blood pressure cuff of claim 10 comprising an image disposed on the sleeve wherein when the folds open the image is substantially revealed.

12. The blood pressure cuff of claim 1 wherein the tension sensor is integral to the sleeve.

13. A cuff, comprising:
   a sleeve including a bladder; and
   a tension sensor integrally coupled to the sleeve.

14. The cuff of claim 13 wherein the tension sensor indicates when a predetermined amount of tension is applied to the tension sensor.

15. The cuff of claim 13 wherein the tension sensor changes appearance when a certain amount of tension is applied to the tension sensor.

16. The cuff of claim 15 wherein the tension sensor is manufactured from an elastic material.

17. The cuff of claim 15 comprising a ridged portion formed in the tension sensor.

18. The cuff of claim 15 comprising an indicator disposed on the ridged portion.

19. The blood pressure cuff of claim 18 wherein the indicator is a graphic, and wherein the indicator is partially hidden when less than a predetermined amount of tension is applied to the tension sensor and wherein the indicator is substantially viewable when more than a predetermined amount of tension is applied to the tension sensor.

20. The cuff of claim 13 wherein the tension sensor includes a set of folds, wherein the when the tension sensor is under less than a pre-set amount of tension the folds are folded, and wherein when the tension sensor is under at least the pre-set amount of tension the folds open.

21. The cuff of claim 20 comprising an image wherein when the folds open the image is substantially revealed.

22. The cuff of claim 13 wherein the tension sensor is integral to the sleeve.

* * * * *